(12) United States Patent
Bhagwat et al.

(10) Patent No.: US 6,429,231 B1
(45) Date of Patent: Aug. 6, 2002

(54) COMPOSITIONS CONTAINING ANTIMICROBIALS AND UREA FOR THE TREATMENT OF DERMATOLOGICAL DISORDERS AND METHODS FOR THEIR USE

(75) Inventors: Dileep Bhagwat, Bronxville, NY (US); Bradley P. Glassman; Daniel Glassman, both of Fairfield, NJ (US)

(73) Assignee: Bradley Pharmaceuticals, Inc., Fairfield, NJ (US)

( * ) Notice: Subject to any disclaimer, the term of this patent is extended or adjusted under 35 U.S.C. 154(b) by 0 days.

(21) Appl. No.: 09/961,576

(22) Filed: Sep. 24, 2001

(51) Int. Cl.[7] ........................... A61K 31/18; A61K 31/17
(52) U.S. Cl. .................. 514/603; 514/588; 514/859
(58) Field of Search ................. 514/603, 433, 514/588, 859; 424/433

(56) References Cited

U.S. PATENT DOCUMENTS

| | | | |
|---|---|---|---|
| 3,983,209 A | | 9/1976 | Schmitt |
| 3,985,873 A | | 10/1976 | Alvan et al. |
| 4,122,158 A | | 10/1978 | Schmitt |
| 4,698,359 A | * | 10/1987 | Niederer et al. |
| 4,895,727 A | | 1/1990 | Allen |
| 5,288,503 A | | 2/1994 | Wood et al. |
| 5,357,636 A | | 10/1994 | Dresdner, Jr. et al. |
| 5,466,463 A | * | 11/1995 | Ford |
| 5,696,101 A | | 12/1997 | Wu et al. |
| 5,716,621 A | | 2/1998 | Bello et al. |
| 5,891,463 A | | 4/1999 | Bello et al. |
| 5,985,795 A | * | 11/1999 | Suganuma |
| 6,036,966 A | | 3/2000 | Youssefyeh |

* cited by examiner

*Primary Examiner*—William R. A. Jarvis
*Assistant Examiner*—Vickie Kim
(74) *Attorney, Agent, or Firm*—Merchant & Gould P.C.

(57) ABSTRACT

Topical compositions which include urea and an antimicrobial agent, particularly sulfacetamide, are described. Sulfacetamide compositions further including sulfur are also described. Methods for treating dermatological disorders using the compositions are also described.

6 Claims, No Drawings

COMPOSITIONS CONTAINING ANTIMICROBIALS AND UREA FOR THE TREATMENT OF DERMATOLOGICAL DISORDERS AND METHODS FOR THEIR USE

FIELD OF THE INVENTION

This present disclosure relates to novel compositions containing antimicrobial agents and urea as components for the treatment of dermatological disorders.

BACKGROUND OF THE INVENTION

There is a need to provide antimicrobial agent compositions, which are easily and economically prepared, which have a smooth texture appropriate for cosmetic products, and which are enhanced by exhibiting greater keratolytic and antimicrobial effects. Compositions containing antimicrobial agents and urea as components and particularly compositions containing sulfacetamide and urea, or sulfacetamide, urea, and sulfur as components might satisfy such a need. Yet such compositions are not currently available.

SUMMARY

The present invention relates to a topical composition that combines the benefits of urea and antimicrobial agents. In one embodiment the topical composition comprises an antimicrobial agent, urea, and a dermatologically acceptable carrier. In another embodiment, the topical composition comprises sulfacetamide or a salt thereof, urea, and a dermatologically acceptable carrier. In yet another embodiment, the topical composition comprises sulfacetamide or a salt thereof, urea, sulfur, and a dermatologically acceptable carrier.

The topical composition of the invention can be useful in treating dermatological disorders. Examples of dermatological disorders that can be treated by the composition include disorders due to microbial infection or changes in normal keratinization, epidermal formation or pilosebaceous function, such as acne, psoriasis, seborrhea, rosacea, ingrown hairs and pseudofolliculitis barbae, and hyperpigmented skin, and cutaneous infection.

In one embodiment, the invention provides a method for treating a dermatological disorder comprising administering to a subject in need thereof a topical composition of the invention. In another embodiment, the invention provides a method for treating acne.

DETAILED DESCRIPTION OF THE INVENTION

Antimicrobial agents and urea are pharmacological agents useful for the treatment of dermatological disorders. However, compositions comprising dermatologically effective amounts of a combination of antimicrobial agents and urea are not currently available. Additionally, compositions comprising dermatologically effective amounts of a combination of sulfacetamide or a salt thereof and urea, and sulfacetamide or a salt thereof and urea optionally with sulfur are not currently available. The current disclosure describes such novel compositions.

Topical Composition

The invention provides topical compositions comprising antimicrobial agents and urea. In one embodiment, the invention provides topical compositions comprising sulfacetamide or a salt thereof and urea. In another embodiment, the invention provides topical compositions comprising sulfacetamide or a salt thereof, urea, and sulfur. The desired amount of active ingredient can vary from composition to composition depending on the particular disorder or disorders being treated, the severity of the disorder, the duration of the treatment, the other specific components of the composition being used, and like factors.

In one embodiment, the antimicrobial agent can be present in the composition at a concentration from about 0.001% to about 20% by weight. In another embodiment, the antimicrobial agent can. be present at a concentration of about 10% by weight.

In one embodiment, the urea can be present in the composition at a concentration from about 0.1% to about 40% by weight, relative to the weight of the composition. In another embodiment, the urea can be present in the composition at a concentration from about 10 to about 40% by weight. In yet another embodiment, the urea can be present in the composition from about 10% to about 20% by weight.

One or more antimicrobial agent agents can be included in the compositions of the invention. As used herein, "antimicrobial agent" or "antimicrobial agent" means an agent that can inhibit the growth of a microorganism or kill a microorganism. Antimicrobial agent agents can have microbial-static effects and/or microbial-cidal effects. Antimicrobial agents can be synthetic compounds, semisynthetic compounds, and naturally produced compounds. As used herein, "antimicrobial agent" refers to both an antimicrobial agent compound and salts thereof. Preferably the antimicrobial agents are dermatologically absorbable. Suitable dermatologically absorbable antimicrobial agents include erythromycin, bacitracin, zinc bacitracin, polymycin, neomycin, chloramphenicol, tetracycline, sulfacetamide, minocycline, clindamycin, doxycycline, undecylenic acid and salts thereof, propionic acid and salts thereof, caprylic acid and salts thereof, ciprofloxacin, cephlasporins, benzoic. acid, ciclopiroxolamine, clotrimazole, econazole nitrate, metronizadole, miconazole nitrate, ketacanazole, oxiconazole, tolnaftate.

In one embodiment, the composition comprises sulfacetamide or a salt thereof and urea. The sulfacetamide salt can be, for example, sodium sulfacetamide. In one embodiment, the composition comprises sulfacetamide or a salt thereof at a concentration in the range of about 5% to 20% by weight, relative to the weight of the composition. In another embodiment, the composition comprises sulfacetamide or a salt thereof at about 10% by weight. In yet another embodiment, the composition comprises urea in the range of about 1% to about 40% by weight, relative to the weight of the composition. In still another embodiment, the composition comprises about 10% to about 40% urea by weight. In another embodiment, the composition comprises urea in a concentration in the range of about 10 to about 20% by weight. In addition to sulfacetamide or a salt thereof and urea, the composition can further comprise sulfur. In one embodiment, the sulfur can be present in the composition at a concentration from about 1% to about 10% by weight, relative to the weight of the composition. In another embodiment, the sulfur can be present at a concentration of about 5% by weight, relative to the weight of the composition.

Any dermatologically acceptable carrier can be used in the compositions of the invention. As used herein, "dermatologically acceptable carrier" refers to vehicles, diluents, carries, which can include adjuvants, additives, or excipients, known for use in dermatological compositions. The compositions of the invention include, but are not limited to, creams, ointments, solutions, lacquers, sticks, pledgets, wipes, cleansers and/or gels.

In one embodiment, the composition is a solution that can be used as a cleanser. In another embodiment, the composition can be used as a lotion.

In yet another embodiment, the topical composition is a semi-solid at room temperature but is easily absorbed into the stratum corneum. The semi-solid composition can be a cream. Such a composition can include petroleum-based liquids and solid fractions as skin protectants. The solid skin protectant can be semi-solid. The solid skin protectant can be present in about 5.5% to about 20% in the composition and includes petrolatum or a synthetic or semi-synthetic hydrocarbon of the same nature as petrolatum. Mixtures of such ingredients can also be used. Liquid skin protectants can be petrolatum and contained in the composition in about 10% to about 20% and include any synthetic or semi-synthetic oleaginous liquid fraction. The liquid skin protectant can be mineral oil, which is a liquid mixture of hydrocarbons obtained from petroleum.

The compositions of the invention can include propylene glycol. Propylene glycol can be present in the composition up to about 10%. In one embodiment, propylene glycol is present in the composition at about 1% to about 5%.

The compositions can contain conventional preservatives, such as methyl paraben, propyl and butyl imidazolidinylurea, diazolidinylurea, methylchloroisothiazolinone and methylisothiazolinone. Although not to be held by theory, it is believed that the antimicrobial properties of the urea and antimicrobial agents and propylene glycol allow the composition of the present invention to be free of conventional preservatives.

The present compositions can also contain dermatologically acceptable excipients, such as for example emulsifiers and thickeners. Among these are for example $C_{16}$ to $C_{18}$ straight or branched chain fatty alcohols or fatty acids or mixtures thereof. Examples of emulsifiers and thickeners include cetyl alcohol, stearyl alcohol, stearic acid, palmitic acid, or mixtures thereof. Fatty acids or fatty alcohols may be present in from about 0.25 to 10 wt-%.

Another ingredient useful in the composition of the present invention may be glyceryl stearate, which is a monoester of glycerine and stearic acid, or other suitable forms of glyceryl stearate for example glyceryl stearate SE, which is a commercially available self-emulsifying grade of glycerol stearate that contains some sodium and/or potassium stearate. Glyceryl stearate may be in the composition anywhere from about 1 to about 10% by weight.

Xanthan gum is another ingredient which may be used in the present compositions. Xanthan gum is a high molecular weight heteropolysaccharide gum produced by pure-culture fermentation of a carbohydrate with *Xanthomonas campestris*. The gum is also commercially available from various sources.

The composition can be an emulsion. The emulsion can contain a fatty phase in the range of about 5% to about 80% by weight. Typically, the fatty phase will range from about 5% to about 50% by weight, with respect to the total weight of the composition. Known oils, waxes, emulsifiers and coemulsifiers can be used in compositions in the emulsion form. The emulsifier and the coemulsifier can be present, in the composition, in a proportion ranging from about 0.3% to about 30% by weight. Typically the emulsifier and the coemulsifier are present in a proportion ranging from about 0.5 to about 20% by weight. The emulsion can also contain lipid vesicles.

In one embodiment, the composition can include thickeners which provide a high viscosity cream designed to remain in place upon application to the skin. By way of example, thickeners can include a mixture of a carbomer and triethanolamine. The mixture can be combined together and added to the composition in an amount totaling anywhere from about 0.05 to 30% by weight. Triethanolamine can be purchased as Trolamine NF from BASF. Carbomers come in various molecular weights and are identified by numbers. These are otherwise known as Carbopol. Exemplary Carbopols include is Carbopol 940, 910, 2984, 5984, 954, 980, 981, 941 and 934. Carbopol ETD 2001, 2020, and 2050 and Ultrez 20 are also commercially available and can be used. The carbomer or Carbopols are resins which are known thickening agents. They are homopolymers of acrylic acid crosslinked with an allyl ether of pentaerythritol, an allyl ether of sucrose or an allyl ether of propylene. The carbomer can be present in the composition as a thickener and also can be used to suspend and stabilize the emulsion.

The composition can also contain known adjuvants and additives, such as bactericides, fungicides, virucides, light filter substances, active ingredients with a cooling action, antioxidants, plant extracts, antiinflammatory, substances which promote wound healing, skin-lightening agents, screening agents, odor absorbers, skin-coloring agents, perfumes, antifoams, dyes, pigments which have a coloring action, thickeners, surface-active substances, emulsifiers, emollients, moisturizers and/or humectants, fats, oils, waxes, alcohols, polyols, polymers, foam stabilizers, electrolytes, organic solvents, silicone derivatives or chelating agents. These additives and adjuvants, depending on their nature, can be introduced into the fatty phase, into the aqueous phase and/or into the lipid spherules.

Exemplary oils or waxes suitable for use in the compositions include mineral oils (liquid petrolatum), vegetable oils (liquid fraction of karite butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. Fatty alcohols and fatty acids (stearic acid) can be added to these oils.

Exemplary emulsifiers which are suitable include glyceryl stearate, polysorbate 60 and the PEG-6/PEG-32/glycol stearate mixture marketed under the trademark Tefose.RTM. 63 by Gattefosse.

Exemplary solvents which can be used in the compositions include the lower alcohols, such as ethanol, isopropanol and propylene glycol.

Exemplary hydrophilic gelling agents suitable for use in the compositions include carboxyvinyl polymers. (carbomer), acrylic copolymers such as acrylate/alkyl acrylate copolymers, polyacrylamides, polysaccharides such as hydroxypropylcellulose, natural gums and clays. And exemplary lipophilic gelling agents include modified clays such as bentones, metal salts of fatty acids such as aluminum stearates, and hydrophobic silica, ethylcellulose or polyethylene.

The compositions can contain other hydrophilic active principles, such as proteins or protein hydrolysates, amino acids, polyols, urea, allantoin, sugars and sugar derivatives, water-soluble vitamins, plant extracts and hydroxy acids.

Representative lipophilic active principles include retinol (vitamin A) and derivatives thereof, tocopherol (vitamin E) and derivatives thereof, essential fatty acids, ceramides, essential oils or salicylic acid and derivatives thereof.

Suitable antioxidants that can be used in the compositions include tocopherols (vitamin E), tocopherol derivatives, tocotrienols, ascorbic acid (vitamin C), ascorbic acid derivatives, carotenoids, vitamin A or derivatives thereof, butylated hydroxytoluene, butylated hydroxyanisole, gallic esters, flavonoids such as, for example, quercetin or myricetin, catechins such as, for example, epicatechin, epicatechingallate, epigallocatechin or epigallocatechingallate, sulfur-containing molecules such as, for example, glutathione, cysteine, lipoic acid, N-acetylcysteine, chelating agents such as, for example, ethylenediamine tetraacetic acid or other customary antioxidants. Antioxidants can be included in the compositions at about 0.0001 to about 30% by weight. Typically antioxidants will be included from about 0.0001 to about 20% by weight. Most often antioxidants will be included from about 0.0001 to about 5% by weight, based on the total weight of the preparation.

Additional keratolytic agents such as salicylic acid and alpha hydroxy acids can be included in the composition.

Dermatological Disorders

The invention provides a method for treating a dermatological disorder comprising administering to a subject in need thereof a topical composition of the invention. As used herein, "treating" or "treatment" means the prevention or reduction of severity of symptoms or effect of a dermatological disorder. A "subject" according to the invention refers to any multicellular organism having skin. Typically, the subject will be a mammal, such as a mouse, a rat, a pig, a horse, a cat, a dog, an elephant, a giraffe, a monkey, or a human, and the like. Typically, the mammal will be a human.

The term "administering" as used herein refers to any method which, in sound medical practice, delivers the composition to a subject in such a manner to so as to be effective in the treatment of a dermatological disorder. The compositions are preferably administered such that they cover the entire area to be treated.

The phrase "safe and effective amount", as used herein, means an amount of a composition or component thereof sufficient enough to positively modify the disorder to be treated but low enough to avoid serious side effects, within the scope of sound medical advice. Safe and effective amounts will vary with the particular disorder or disorders being treated, the severity of the disorder, the duration of the treatment, the specific components of the composition being used, and like factors as are known by health-care providers, including physicians.

As used herein, "dermatological disorder" refers to any disorder of skin, hair, or glands. A dermatological disorder can be manifest in the form of visible lesions, pre-emergent lesions, pain, sensitivity to touch, irritation, inflammation, or the like. Dermatological disorders include disorders of the cutaneous and pilosebaceous unit or the process of keratogenesis. For example, a dermatological disorder can be disorder of the epidermis or dermis, or within and surrounding the pilosebaceous follicle, which is located within the skin's epidermis, dermis, or both. Examples of dermatological disorders include acne, psoriasis, seborrhea, ingrown hairs and pseudofolliculitis barbae, and hyperpigmented skin, cutaneous infections, and the like.

The invention provides a composition comprising an antimicrobial agent and urea. Accordingly, the compositions can be useful for treating dermatological disorders for which an antimicrobial agent or urea are known to be useful. Urea has been long recognized as a cosmetic ingredient in formulations acting as a humectant and moisturizer. Urea also has keratolytic activity and has the property of denaturing and solubilizing proteins. Keratolytic agents are agents that can remove or sluff dead cells of the horny outer layer of the skin (stratus corneum), which are composed largely of keratin. Such agents can prevent obstruction of follicular ducts or reopen obstructed ducts. Additionally, urea, like antimicrobial agents, has antimicrobial activity. It has been found that the combination provides synergistic antimicrobial activity. Thus, the compositions can be useful for treating dermatological disorders in which a humectant, moisturizer, keratolytic agent, antimicrobial agent, protein denaturant or solubilizer, or a combination thereof would be beneficial. Such disorders include any disorder involving obstruction of a follicular duct or bacterial infection. Such disorders include acne, burns, varicose ulcers, sycosis vulgaris and seborrhea.

The compositions of the invention can be used to treat dermatological disorders resulting in visible lesions. Examples of such disorders include acne, cutaneous infections, rosacea, psoriasis and other disorders of the cutaneous and pilosebaceous unit or the process of keratogenesis. Visible lesions include closed comedones, open comedones, red or pustular-looking inflamed papules, pustules, nodules and cysts of acne or cutaneous infection; visible ingrown hairs of pseudofolliculitis barbae; visible scales of seborrhea, ichthyosis and psoriasis; and the like. Visible lesions can be due to obstruction of follicular ducts, thickened sebum, bacterial infection, or a combination thereof. Accordingly, the compositions can be used to prevent obstruction of follicular ducts, to reopen a duct if it has become blocked, to combat thickened sebum, to combat bacterial infection, or a combination thereof. Treatment of visible lesions can be evaluated based on the effectiveness of the treatment in reducing the number and severity of visible lesions. Any reduction in number or severity of visible lesions as a result of administration a composition would be considered treatment of visible lesions.

In one embodiment, the compositions of the invention can be used to treat pre-emergent lesions. As used herein, "pre-emergent lesions" refers to non-visible lesions present within the skin prior to eruption of visible lesions on the surface of the skin. Like visible lesions, pre-emergent lesions can be due to obstruction of follicular ducts, thickened sebum, bacterial infection, or a combination thereof. Accordingly, the compositions can be used to treat pre-emergent lesions by preventing obstruction of follicular ducts, reopening a duct if it has become blocked, combating thickened sebum, combating bacterial infection, or a combination thereof. While pre-emergent lesions are insufficiently visible to be graded in conventional clinical studies, their presence within the skin can be discerned by the tactile sense of feel and/or by pain and tension within the skin. Any reduction in number of locations within the skin in which pre-emergent lesions exist as a result of administration of a composition would be considered treatment of pre-emergent lesions. Similarly, any reduction in the severity of the symptoms of a pre-emergent lesion as a result of administration of a composition would be considered treatment of the pre-emergent lesion.

In another embodiment, the compositions of the invention can be used to treat acne. As used herein, "acne" means a disorder of the skin caused by inflammation of skin glands or hair follicles. The compositions of the invention can be used to treat acne at early pre-emergent stages or later stages where lesions from acne are visible. Early pre-emergent stages of acne usually begins with an excessive secretion of sebum or dermal oil from the sebaceous glands located in the pilosebaceous apparatus. Sebum reaches the skin surface through the duct of the hair follicle. The presence of excessive amounts of sebum in the duct and on the skin tends to obstruct or stagnate the normal flow of sebum from the follicular duct, thus producing a thickening and solidification of the sebum to create a solid plug known as a comedone. In the normal sequence of developing acne, hyperkeratinazation of the follicular opening is stimulated, thus completing blocking of the duct. The usual results are papules, pustules, or cysts, often contaminated with bacteria, which cause secondary infections. Acne is characterized particularly by the presence of comedones, inflammatory papules, or cysts. The appearance of acne may range from slight skin irritation to pitting and even the development of disfiguring scars. Accordingly, the compositions of the invention can be used to treat skin irritation, pitting, development of scars, comedones, inflammatory papules, cysts, hyperkeratinazation, and thickening and hardening of sebum associated with acne and rosacea.

All patent and literature references cited in the present specification are hereby incorporated by reference in their entirety. All parts and percentages are by weight unless otherwise specified. All scientific and technical terms used in this application have meanings commonly used in the art unless otherwise specified.

EXAMPLES

The following examples are offered for illustrative purposes only, and are not intended to limit the scope of the present invention in any way.

Example 1

Preparation of Formula I, an Exemplary Composition

Formula I is a cleanser composed of the ingredients shown in Table 1 and was prepared using the following protocol.

TABLE 1

| Ingredient Number | Component | Weight % |
|---|---|---|
| 1 | Purified Water | 24.695 |
| 2 | Propylparaben | 0.015 |
| 3 | Methylparaben | 0.150 |
| 4 | Edetate Disodium | 0.100 |
| 5 | Butylated Hydroxytoluene | 0.100 |
| 6 | Sodium Methyl Cocoyl Taurate | 4.200 |
| 7 | Sodium Cocoyl Isothionate | 3.00 |
| 8 | Purified Water | 18.00 |
| 9 | Magnesium Aluminum Silicate | 1.00 |
| 10 | Xanthan Gum | 0.090 |
| 11 | Sodium Sulfacetamide | 10.200 |
| 12 | Purified Water | 1.000 |
| 13 | Cetyl Alcohol | 2.800 |
| 14 | Stearyl Alcohol | 2.400 |
| 15 | Glyceryl Stearate (and) PEG-100 Stearate | 2.800 |
| 16 | Purified Water | 1.00 |
| 17 | Disodium Oleamino PEG-2 Sulfocinate | 3.200 |
| 18 | Precipitated Sulfur | 5.000 |
| 19 | Purified Water | 1.000 |
| 20 | Purified Water | 0.100 |
| 21 | Sodium Thiosulfate | 0.100 |
| 22 | Purified Water | 0.300 |
| 23 | Urea | 10.200 |
| 24 | Purified Water | 10.200 |
| 25 | Purified Water | 1.250 |
| 26 | Fragrance | 0.100 |
| | Total | 103* |

*contains a 3% manufacturing excess

Equipment Used

Stainless steel mixing Tank A and B

Transfer pumps

Stainless Steel (S.S.) Containers

Colloid Mill

Manufacturing Procedure

I. Into tank A, add ingredient #1 and heat to about 70° C. Once the temperature is achieved add ingredient #2, 3, and 4. Mix until completely dissolved.

II. Into tank A add ingredients #5, 6, and 7. Mix until complete dissolution while maintaining temperature at about 70° C.

III. Into a S.S. container of appropriate size, add ingredient #8 and heat to about 40° C. Sprinkle ingredient #9 and #10. Once dissolution is obtained, add ingredient #11 and mix until complete dissolution.

IV. Transfer phase made at previous step (III) into tank A. Mix until the mixture is homogeneous.

V. In Tank B, melt ingredients #13, 14, and 15 at about 70° C. while agitating. Add the mixture to tank A. Mix until homogenous.

VI. Cool down mixture to about 40° C.

VII. Into a stainless steel container or appropriate size, disperse ingredient #18 in ingredient #17, if necessary add a portion of ingredient #19 to improve dispersion. Once the mixture is homogenous transfer it into tank A. Rinse the container with the remaining of ingredient #19; add to tank A. Mix until homogeneity is observed. Maintain the temperature at about 40° C.

VIII. Into a S.S. container, dissolve ingredient #21 in ingredient #20. Add solution to tank A. Rinse container using ingredient #22 and add to tank A. Mix until homogeneous.

IX. In a S.S. container, dissolve ingredient #23 in ingredient #24; heat if necessary. Transfer the solution into tank A. Mix for about 15 minutes minimum while maintaining temperature at about 40° C.

X. Into tank A, add ingredient #26 and mix for 15 minutes minimum.

XI. Mill the product through a suitable colloid mill.

XII. Cool down product to room temperature.

Example 2

Preparation of Formula II, an Exemplary Composition

Formula II is a lotion composed of the ingredients shown in Table 2 and was prepared using the following protocol.

TABLE 2

| Ingredient Number | Component | Weight % |
|---|---|---|
| 1 | Purified Water | 12.95 |
| 2 | Edetate Disodium | 0.10 |
| 3 | Xanthan Gum | 0.10 |
| 4 | Propylene Glycol | 4.00 |
| 5 | Isopropyl Myristate | 5.00 |
| 6 | Light Mineral Oil | 4.00 |
| 7 | Sorbitan Monostearate | 3.00 |
| 8 | Cetyl Alcohol | 2.80 |
| 9 | Cocoglycerides | 2.60 |
| 10 | Stearyl Alcohol | 2.40 |
| 11 | Glyceryl Sterate/PEG-100 Stearate | 2.00 |
| 12 | Dimethicone 200/100 | 0.40 |
| 13 | Zinc Ricinoleate | 0.10 |
| 14 | Purified Water | 0.30 |
| 15 | Propylene Glycol | 10.00 |
| 16 | Polysorbate 60 | 3.50 |
| 17 | Precipitated Sulfur | 5.10 |
| 18 | Propylene glycol | 1.00 |
| 19 | Purified Water | 10.20 |
| 20 | Sodium Sulfacetamide | 10.20 |
| 21 | Sodium Thiosulfate | 0.10 |

TABLE 2-continued

| Ingredient Number | Component | Weight % |
|---|---|---|
| 22 | Purified Water | 0.30 |
| 23 | Urea | 10.20 |
| 24 | Purified Water | 10.20 |
| 25 | Purified Water | 0.30 |
| 26 | Benzyl Alcohol | 2.00 |
| 27 | Fragrance | 0.15 |
|  | Total | 103* |

*contains a 3% manufacturing excess

Example of Equipment Used
Tank A (stainless steel mixing tank)
Tank B (stainless steel mixing tank)
Transfer pump
Stainless Steel (S.S.) Containers
Colloid mill
Manufacturing Procedure I. Into tank A, add ingredient #1 and then ingredient #2. Heat to about 70° C. Mix until completely dissolved.

II. Into an appropriate size S.S. container disperse ingredient #3 into ingredient #4. Mix until a homogeneous mixture is obtained. Add mixture into tank A while maintaining temperature of about 70±2° C. Mix for 15 minutes minimum.

III. Into tank B, add ingredients #5, 6, 7, 8, 9, 10, 11, 12, and 13. Melt at about 70° C. and mix until mixture is homogenous.

IV. Transfer phase made at previous step (III, tank B) into tank A. Rinse container using ingredient #14 and add to tank A. Mix until the mixture is homogeneous. Use turbine if necessary in order to obtain an adequate emulsion.

V. Cool down mixture to about 45° C. while mixing.

VI. Into an appropriate size S.S. container, add ingredients #15 and 16. Heat at 30–35° C. and mix until homogenous. Disperse ingredient #17 in mixture, if necessary add a portion of ingredient #18 to improve dispersion. Once the mixture is homogenous transfer it into tank A. Rinse the container with the remaining of ingredient #18 and add to tank A. Mix until homogeneity is observed. Maintain temperature at about 45° C.

VII. Into an S.S. container, dissolve ingredients #20 and 21 into ingredient #19. Add solution to tank A. Rinse container using ingredient #22 and add to tank A. Mix until homogeneous. Maintain temperature at about 45° C.

VIII. In a S.S. container, dissolve ingredient #23 in ingredient #24, heat if necessary. Transfer the solution into tank A. Rinse the container using ingredient #25 and add to tank A. Mix for 15 minutes minimum while maintaining temperature at about 45° C.

IX. Into tank A, add ingredients #26 and 27. Mix for 15 minutes minimum.

X Cool down product to room temperature.

Although the present invention has been described in terms of specific embodiments, changes and modifications can be carried out without departing from the scope of the invention which is intended to be limited only by the scope of the appended claims.

We claim:

1. A topical composition for treatment of dermatological disorders consisting essentially of:
    (a) a dermatologically effective amount of sulfacetamide or a salt thereof;
    (b) about 10 to about 40% by weight of urea;
    (c) sulfur; and
    (d) a dermatologically acceptable carrier.

2. The composition of claim 1, wherein the composition comprises about 1 to about 10% by weight sulfur.

3. The composition of claim 1, wherein the composition comprises about 5% by weight sulfur.

4. A method for treating a dermatological disorder comprising administering to a subject in need thereof a topical composition according to claim 1.

5. The method of claim 4, wherein the dermatological disorder is selected from the group consisting of acne, psoriasis, seborrhea, rosacea, ingrown hairs, pseudofolliculitis barbae, hyperpigmented skin, and cutaneous infection.

6. The method of claim 4, wherein the dermatological disorder is acne.

* * * * *

(12) INTER PARTES REEXAMINATION CERTIFICATE (746th)
United States Patent
Bhagwat et al.

(10) Number: US 6,429,231 C1
(45) Certificate Issued: Nov. 22, 2013

(54) COMPOSITIONS CONTAINING ANTIMICROBIALS AND UREA FOR THE TREATMENT OF DERMATOLOGICAL DISORDERS AND METHODS FOR THEIR USE

(75) Inventors: Dileep Bhagwat, Bronxville, NY (US); Bradley P. Glassman, Fairfield, NJ (US); Daniel Glassman, Fairfield, NJ (US)

(73) Assignee: Wachovia Bank, National Association, Charlotte, NC (US)

Reexamination Request:
No. 95/000,319, Jan. 7, 2008

Reexamination Certificate for:
Patent No.: 6,429,231
Issued: Aug. 6, 2002
Appl. No.: 09/961,576
Filed: Sep. 24, 2001

(51) Int. Cl.
*A61K 8/30* (2006.01)
*A61K 8/46* (2006.01)
*A61Q 19/02* (2006.01)
*A61Q 5/00* (2006.01)
*A61Q 9/00* (2006.01)
*A61Q 19/00* (2006.01)

(52) U.S. Cl.
USPC .............................. 514/603; 514/588; 514/859

(58) Field of Classification Search
None
See application file for complete search history.

(56) References Cited

To view the complete listing of prior art documents cited during the proceeding for Reexamination Control Number 95/000,319, please refer to the USPTO's public Patent Application Information Retrieval (PAIR) system under the Display References tab.

*Primary Examiner* — Dwayne Jones

(57) ABSTRACT

Topical compositions which include urea and an antimicrobial agent, particularly sulfacetamide, are described. Sulfacetamide compositions further including sulfur are also described. Methods for treating dermatological disorders using the compositions are also described.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-6 are cancelled.

\* \* \* \* \*